(12) United States Patent
Lee et al.

(10) Patent No.: US 11,389,411 B2
(45) Date of Patent: Jul. 19, 2022

(54) PHARMACEUTICAL COMPOSITION, CONTAINING NM23 ACTIVATOR, FOR INHIBITING CANCER METASTASIS

(71) Applicant: EWHA UNIVERSITY—INDUSTRY COLLABORATION FOUNDATION, Seoul (KR)

(72) Inventors: Kong Joo Lee, Seoul (KR); Hee-Yoon Lee, Daejeon (KR); Je Jin Lee, Seoul (KR); Eun-Kyoung Seo, Seoul (KR); Eun Sun Lee, Seoul (KR); Hwang Suk Kim, Gyeonggi-do (KR); Hongsoo Lee, Daejeon (KR)

(73) Assignee: EWHA UNIVERSITY—INDUSTRY COLLABORATION FOUNDATION, Seoul (KR)

( * ) Notice: Subject to any disclaimer, the term of this patent is extended or adjusted under 35 U.S.C. 154(b) by 23 days.

(21) Appl. No.: 16/609,094

(22) PCT Filed: Apr. 30, 2018

(86) PCT No.: PCT/KR2018/005036
§ 371 (c)(1),
(2) Date: Oct. 28, 2019

(87) PCT Pub. No.: WO2018/199727
PCT Pub. Date: Nov. 1, 2018

(65) Prior Publication Data
US 2020/0078319 A1 Mar. 12, 2020

(30) Foreign Application Priority Data

Apr. 28, 2017 (KR) .................. 10-2017-0055151
Apr. 27, 2018 (KR) .................. 10-2018-0049329

(51) Int. Cl.
*A61K 31/09* (2006.01)
*A61P 35/04* (2006.01)

(52) U.S. Cl.
CPC .............. *A61K 31/09* (2013.01); *A61P 35/04* (2018.01)

(58) Field of Classification Search
CPC .................................................. A61K 31/09
See application file for complete search history.

(56) References Cited

PUBLICATIONS

Matsuda et al., Invasion Inhibitors of Human Fibrosarcoma HT 1080 Cells from the Rhizomes of Zingiber cassumunar: Structures of Phenylbutanoids, Cassumunols, Chem. Pharm. Bull. 59(3) 365-370 (2011).*
Han et al., A New Cytotoxic Phenylbutenoid Dimer from the Rhizomes of Zingiber cassumunar, Planta Med 2004; 70: 1095-1097.*
Zhao et al., Compounds from *Dryopteris fragrans* (L.) Schott with Cytotoxic Activity, Molecules 2014, 19, 3345-3355.*
Zhao. D.-D. et al., "Compounds from *Dryopteris fragrans* (L.) Schott with Cytotoxic Activity", Molecules, 2014, vol. 19, pp. 3345-3355.
Chae, S.W. et al., "In Vitro and in Vivo Evaluation of Phenylbutenoid Dimers as Inhibitors of P-gylcoprotein", Journal of Natural Products, Nov. 22, 2013, vol. 76, pp. 2277-2281.
Matsuda, H. et al., "Invasion Inhibitors of Human Fircosarcoma HT 1080 Cells from the Phizomes of Zingiber Cassumunar: Structures of Phenylbutanoids, Cassumunols", Chemical and Pharmaceutical Bulletin, Mar. 2011, vol. 59, No. 3, pp. 365-370.
Chung, S.Y. et al., "Potent Modulation of P-glycoprotein Activity by Naturally Occurring Phenylbutenoids from Zingiber Cassumunar", Phytotherapy Research, 2009, vol. 23, No. 4, pp. 472-476.
Kuroyanagi, M. et al., "Further Characterization of the Constituents of a Thai Medicinal Plant, Zingiber Cassumunar Roxb", Chemical and Pharmaceutical Bulletin, 1980, vol. 28, pp. 2948-2959.
Horack CE et al., "The role of metastatis suppressor genes in metastatic dormancy", APMIS. Jul.-Aug. 2008; 116 (7-8):586-601.
Lee, E. et al., "Multiple functions of Nm23-H1 are regulated by oxido-reduction system", PLoS One. (2009) Nov. 23, 2009; 4(11):e7949, pp. 1-14.
Palmieri D. et al., "Medroxyprogesterone acetate elevation of Nm23-H1 metastasis suppressor expression in hormone-receptor-negative breast cancer", J Natl Cancer Inst., May 4, 2005; 97(9):632-42.
Lim J. et al., "Cell-permeable NM23 blocks the maintenance and progression of established pulmonary metastasis", Cancer Research (2001) Dec. 1, 2001;71 (23): 7216-25.
International Search Report International Application No. PCT/KR2018/005036 dated Aug. 16, 2018, 3 pages.
Supplementary European Search Report issued in EP 18789847.3 dated Dec. 7, 2020.
Office Action issued in Indian Application No. 201917046350 dated May 13, 2020.
Jong-Won Lee et al., "Growth Inhibition and Induction of G1 Phase Cell Cycle Arrest in Human Lung cancer Cells by a Phenylbutenoid Dimer Isolated from Zingiber cassumunar", Biol. Pharm. Bull., vol. 30, No. 8, pp. 1561-1564, Aug. 2007.
Shuya Yano et al., "Invading Cancer Cells are Predominantly in G0/G1 Resulting in Chemoresistance Demonstrated by Real-Time FUCCI Imaging", Cell Cycle, vol. 13, No. 6, pp. 953-960, Jan. 20, 2020.

(Continued)

Primary Examiner — Svetlana M Ivanova
(74) Attorney, Agent, or Firm — DLA Piper LLP US

(57) ABSTRACT

The present disclosure relates to a pharmaceutical composition for suppressing cancer metastasis containing, as an active ingredient, an activator compound of the cancer metastasis inhibitor Nm23, a stereoisomer thereof, or a pharmaceutically acceptable salt thereof. The compound according to the present disclosure may suppress the metastasis of cancer cells by promoting the activity of Nm23 associated with cancer metastasis, and thus may be useful as a pharmaceutical composition for suppressing cancer metastasis.

4 Claims, 10 Drawing Sheets

(56) References Cited

PUBLICATIONS

Dan-Dan Zhao et al., "Compounds from *Dryopteris fragrans* (L.) Schott with Cytotoxic Activity", Molecules, vol. 19, pp. 3345-3355 (2014).
Abstract of Song Wha Chae et al., "In Vitro and in Vivo Evaluation of Phenylbuteniod Dimers as Inhibitors of P-Glycoprotein", J. Natl., Prod., vol. 76, No. 12, pp. 2277-2281, Nov. 22, 2013.

* cited by examiner

Fig. 5A-B

Fig. 6
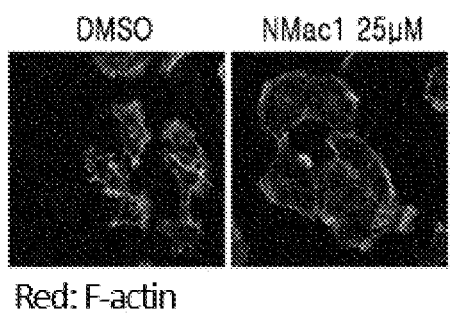
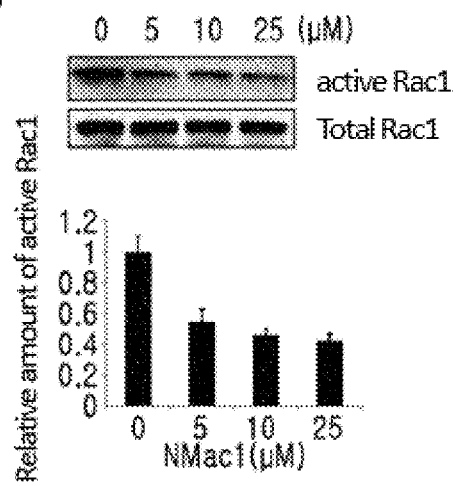
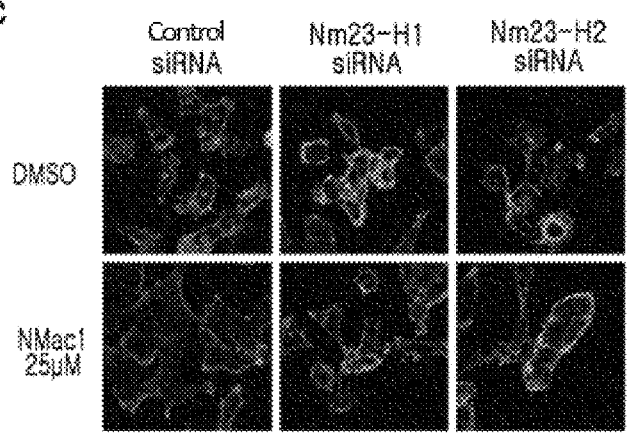
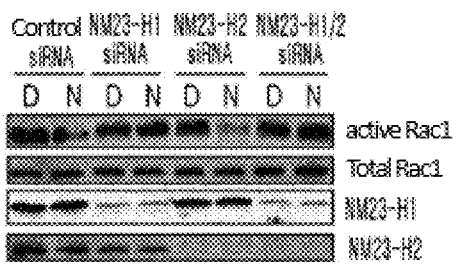
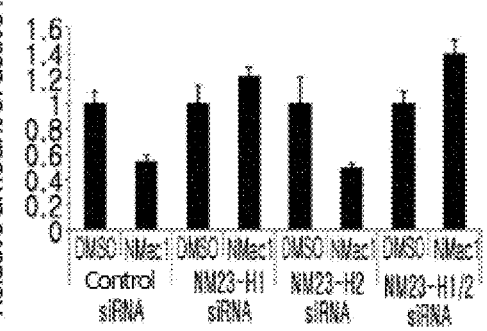

PHARMACEUTICAL COMPOSITION, CONTAINING NM23 ACTIVATOR, FOR INHIBITING CANCER METASTASIS

TECHNICAL FIELD

The present disclosure relates to a pharmaceutical composition for suppressing cancer metastasis containing a novel Nm23 activator.

BACKGROUND ART

Cancer metastasis is one of the most important factors determining the prognosis of cancer patients and is the main process that determines death caused by cancer. In cancer therapies such as surgery, radiotherapy, chemotherapy and the like, a lot of efforts have been made to improve the survival of patients, but efforts have still been made to improve the survival of cancer patients. The field of studying cancer metastasis is one of the last strategies to overcome cancer, and studies on cancer metastasis suppressors are essential for developing metastasis-suppressing drugs.

Nm23 is a gene encoding a protein involved in the development and differentiation of normal tissue, and the expression of Nm23 has been reported to decrease in various metastatic cell lines. In general, Nm23 protein consisting of 150 to 180 amino acids comprises a leucine zipper motif and has a dinucleotide phosphate kinase (NDPK) activity. In particular, Nm23-H1 has been shown to play an important role in cancer metastasis and various other cellular mechanisms, for example, proliferation, embryonic development, differentiation, tumor formation, and the like. FIG. 1 is a view showing the stages of cancer metastasis. The metastasis of cancer occurs through a series of sequential stages in which cancer cells in the primary tumor invade blood vessels, travel through the blood vessels, survive and form new colonies at secondary sites. Referring to FIG. 1, it can be seen that Nm23-H1 is involved in cancer metastasis suppressing activity at various stage of the cancer metastasis process, such as invasion/intravasation, extravasation, metastatic colonization, etc. (Horak C E, et al., The role of metastasis suppressor genes in metastatic dormancy, APMIS. (2008) July-August; 116(7-8):586-601).

The mechanism by which Nm23 affects cancer metastasis and development has not yet been clearly found, but as NDPK (nucleotide diphosphate kinase), but it has been found that Nm23 is a nucleotide diphosphate kinase (NDPK) protein, an enzyme that converts NDP (UDP, GDP, CDP) into NTP (UTP, GTP, CTP) using ATP and regulates the intracellular level of NTP. FIG. 2 is a schematic diagram showing the NDPK activity of Nm23. In addition, overexpression of Nm23-H1 has been found to be closely associated with decreased cancer cell invasion (Lee E, et al., Multiple functions of Nm23-H1 are regulated by oxido-reduction system, PLoS One. (2009) Nov. 23; 4(11):e7949).

Based on these findings, studies have been conducted to increase the expression of Nm23 or to treat cells with cell permeable Nm23-H1. Specifically, it was confirmed that treatment with MPA (medroxyprogesterone acetate) increases the expression level of Nm23-H1, and this phenomenon is understood as a mechanism of suppressing cancer metastasis by MPA treatment (Palmieri D et al., Medroxyprogesterone acetate elevation of Nm23-H1 metastasis suppressor expression in hormone receptor-negative breast cancer, J Natl Cancer Inst. (2005) May 4; 97(9):632-42). Since MPA treatment causes unexpected intracellular responses in addition to increasing the level of Nm23-H1, MPA has not been used as a drug.

Moreover, in recent years, a method of suppressing cancer metastasis using a cell permeable Nm23-H1 has been proposed (Lim J, et al., Cell-permeable NM23 blocks the maintenance and progression of established pulmonary metastasis. Cancer Res. (2011) Dec. 1; 71 (23): 7216-25). Cell-permeable Nm23-H1 was introduced into cells after fusing it with a transporter peptide that can pass through the plasma membrane. As a result, it was confirmed that treatment with cell-permeable Nm23-H1 exhibited cancer metastasis suppressing activity. However, in order for such cell-permeable Nm23-H1 to be applied as a protein drug, the in vivo stability thereof remains as a challenge to be overcome, and since cancer metastasis suppressing drugs show no significant effect when they are used for treatment for a short period of time, there is a practical problem in that a high-cost drug such as a protein drug cannot be chosen.

DISCLOSURE

Technical Problem

The present inventors have conducted research and development on a small molecule substance that modulates the activity of Nm23 involved in the cancer metastasis process, thereby completing the present disclosure.

Technical Solution

It is an object of the present disclosure to provide a pharmaceutical composition for cancer metastasis containing a novel Nm23 activator.

Advantageous Effects

A pharmaceutical composition of the present disclosure, which contains, as an active ingredient, a compound represented by Formula 1, a stereoisomer thereof, or a pharmaceutically acceptable salt thereof, acts as an activator of Nm23-H1 and/or Nm23-H2 and suppresses the metastasis and invasion of cancer cells. Therefore, the Nm23 activator according to the present disclosure can be very useful as a pharmaceutical composition for suppressing metastasis of cancer.

DESCRIPTION OF DRAWINGS

FIG. 6 panels A-E show the results obtained by treating two types of breast cancer cell lines with a compound of Formula 2-1, observing the morphological changes of the cells and observing Rac1 activity in each of the cell lines.

BEST MODE

Figure 1:
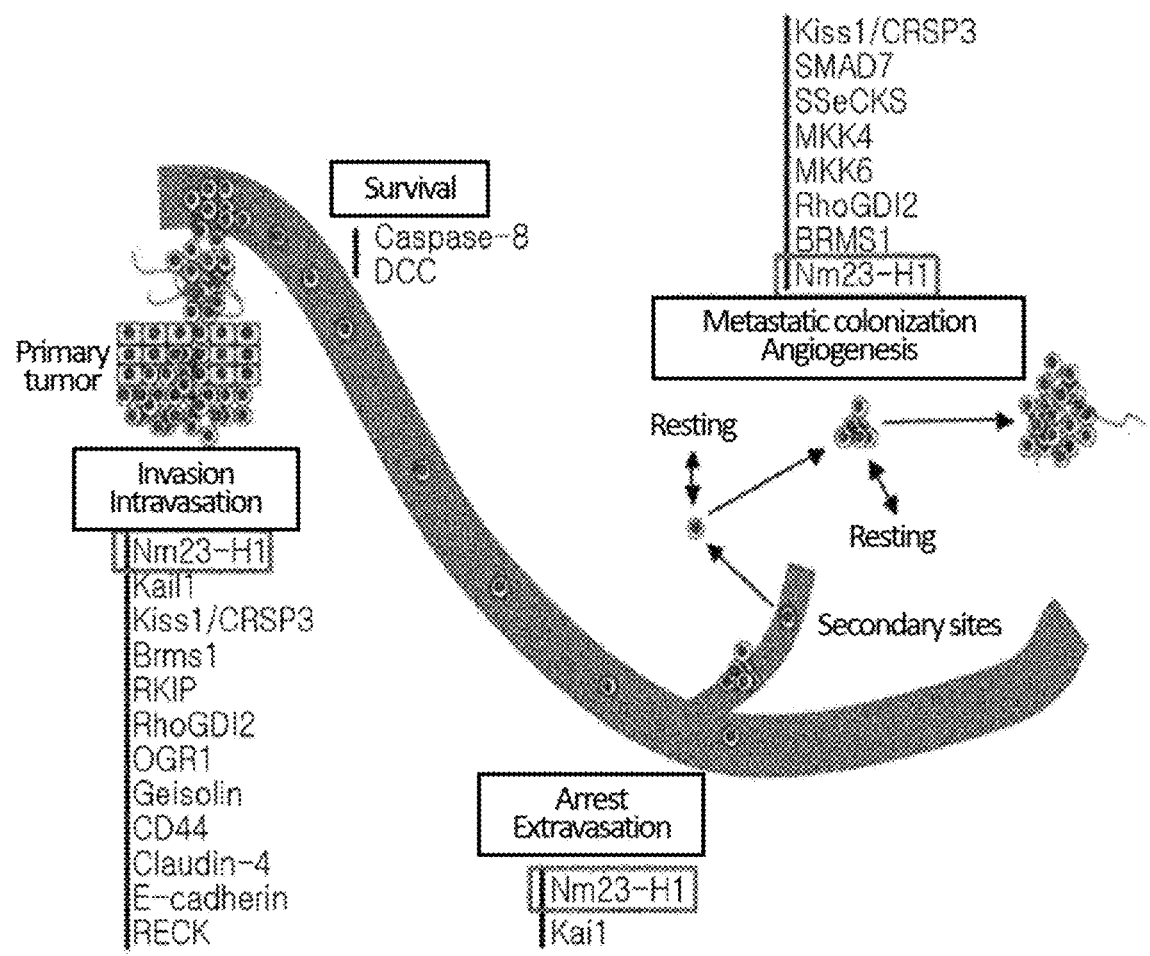
FIG. 1 is a schematic view showing cancer metastasis stages.
Figure 2:
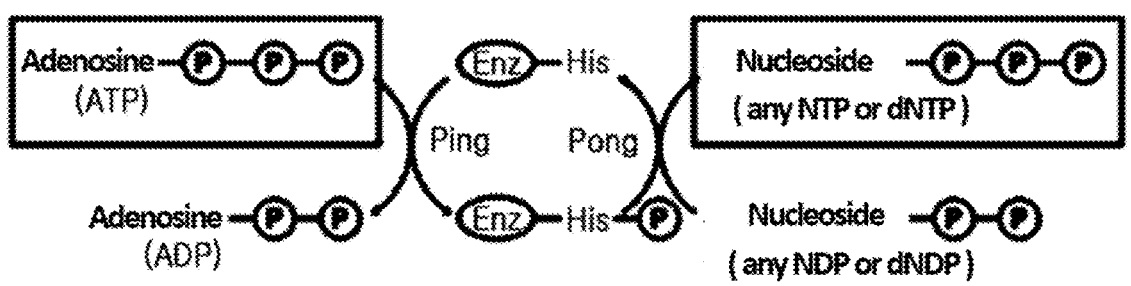
FIG. 2 is a schematic view showing the NDPK activity of Nm23.

The present inventors have identified compounds that increase the NDPK activity of Nm23, thereby completing the present disclosure.

Hereinafter, the present disclosure will be described in more detail.

Throughout the present specification, it is to be understood that when any part is referred to as "comprising" or "containing" any component, it does not exclude other components, but may further comprise other components, unless otherwise specified.

One aspect of the present disclosure is directed to a pharmaceutical composition for suppressing cancer metastasis containing, as an active ingredient, a compound represented by the following Formula 1, a stereoisomer thereof, or a pharmaceutically acceptable salt thereof:

[Formula 1]

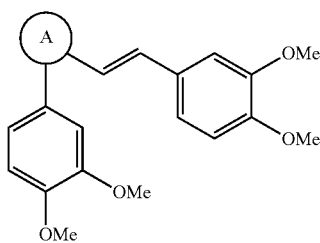

wherein ring A is cyclohexene, cyclohexane or benzene.

In one embodiment of the present disclosure, the compound represented by Formula 1 is a compound represented by any one of the following Formulas 2 to 4:

[Formula 2]

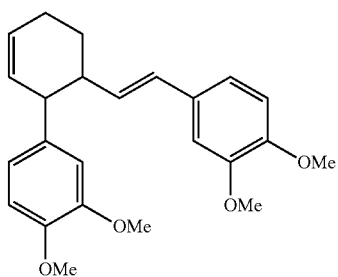

[Formula 3]

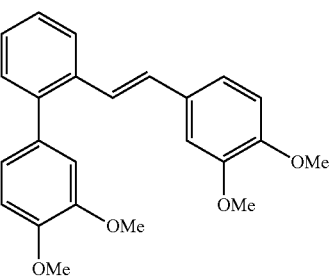

[Formula 4]

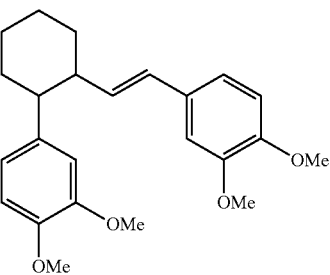

In the present disclosure, the stereoisomer may exist as an optical isomer, a racemate, a racemic mixture, a single enantiomer, a diastereomeric mixture, or each diastereomer. This isomer can be separated by a conventional technique, for example, resolution using column chromatography or HPLC. Alternatively, the stereoisomer of the compound represented by Formula 1 may be stereospecifically synthesized using optically pure starting materials and/or reagents whose configurations are known.

In another embodiment of the present disclosure, the stereoisomer of the compound represented by Formula 1 has an E form.

In one embodiment of the present disclosure, the compound represented by Formula 1 may be any one of the following Formulas 2-1 to 4-1:

[Formula 2-1]

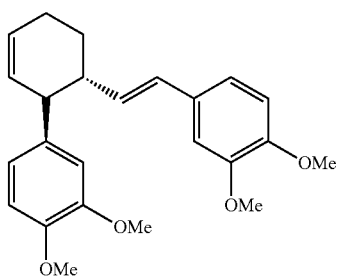

[Formula 3-1]

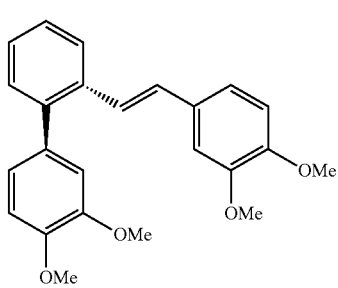

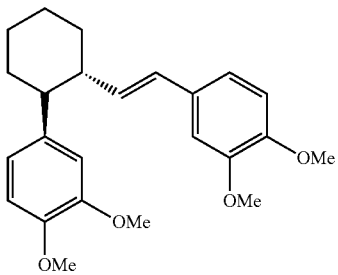

[Formula 4-1]

The compounds of Formulas 2-1 to 4-1 may be produced, for example, by the process described in Preparation Examples 1 to 3 of the present disclosure, but are not limited thereto.

In the present disclosure, the pharmaceutically acceptable salt refers to salts which are commonly used in the pharmaceutical field, and examples thereof include inorganic ion salts formed with calcium, potassium, sodium, magnesium, etc.; inorganic acid salts formed with hydrochloric acid, nitric acid, phosphoric acid, bromic acid, iodic acid, perchloric acid, sulfuric acid, etc.; organic acid salts formed with acetic acid, trifluoroacetic acid, citric acid, maleic acid, succinic acid, oxalic acid, benzoic acid, tartaric acid, fumaric acid, manderic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, etc.; sulfonic acid salts formed with methanesulfonic acid, ethanesulfonic acid, benzenesulfonic acid, p-toluenesulfonic acid, naphthalenesulfonic acid, etc.; amino acid salts formed with glycine, arginine, lysine, etc.; and amine salts formed with trimethylamine, triethylamine, ammonia, pyridine, picoline, etc., but the types of salts in the present disclosure are not limited to these listed salts.

Figure 3:
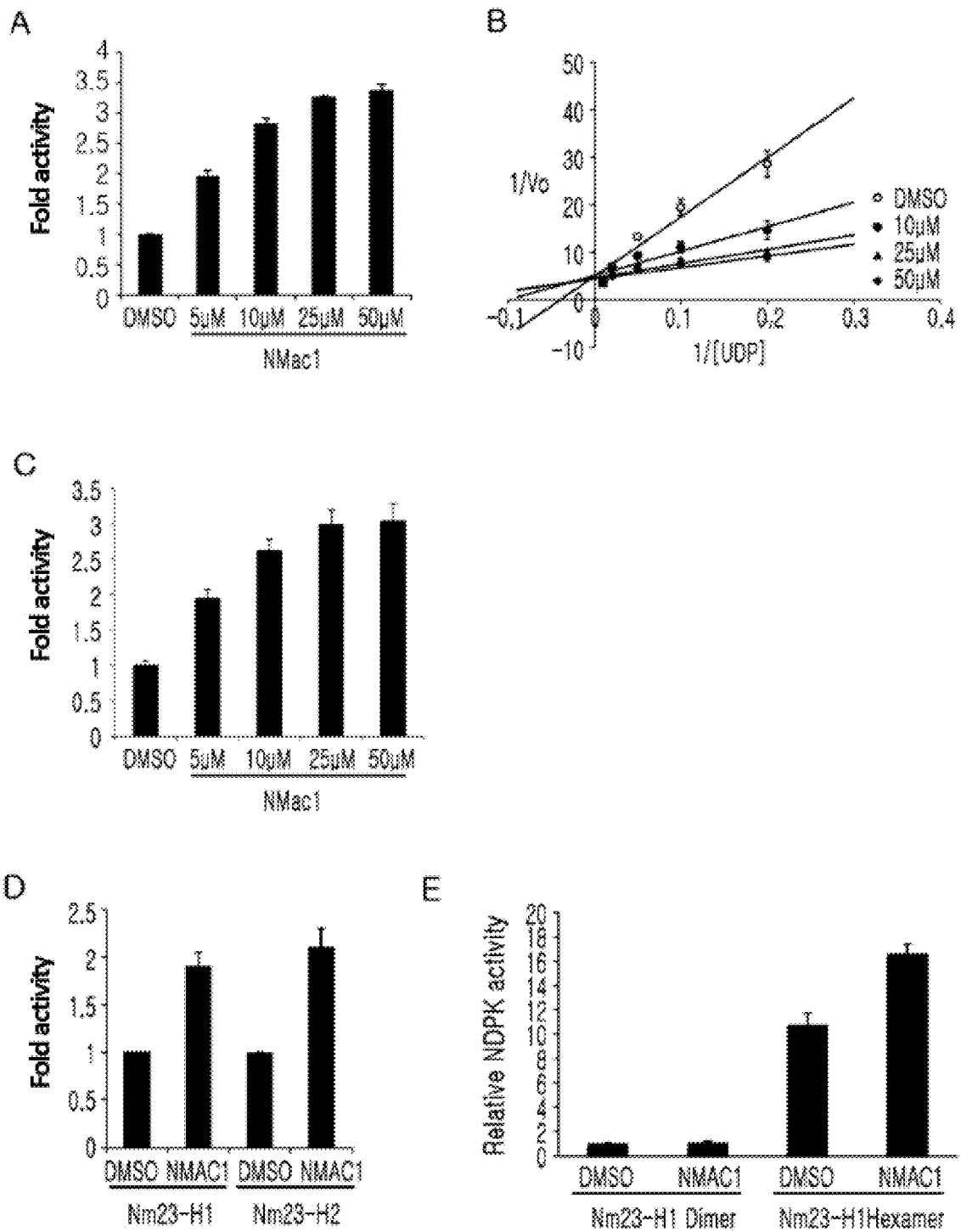
FIG. 3 panels A-E show the results of analyzing NDPK activity for a compound of Formula 2-1.

In addition, the pharmaceutical composition of the present disclosure may act as an activator of Nm23-H1, an activator of Nm23-H2 or an activator of Nm23-H1 and Nm23-H2. Specifically, the compound of Formula 1 according to the present disclosure may form a hydrophobic pocket by interaction with Nm23-H1, thus controlling the exposure of the active site and the kpn-loop known to play the most important role in the regulation of NDPK activity and allosterically increasing NDPK activity. Furthermore, the compound of Formula 1 according to the present disclosure may also exhibit the same activity on Nm23-H2 which is another subtype of Nm23 (FIG. 3 and Table 2).

Figure 4:
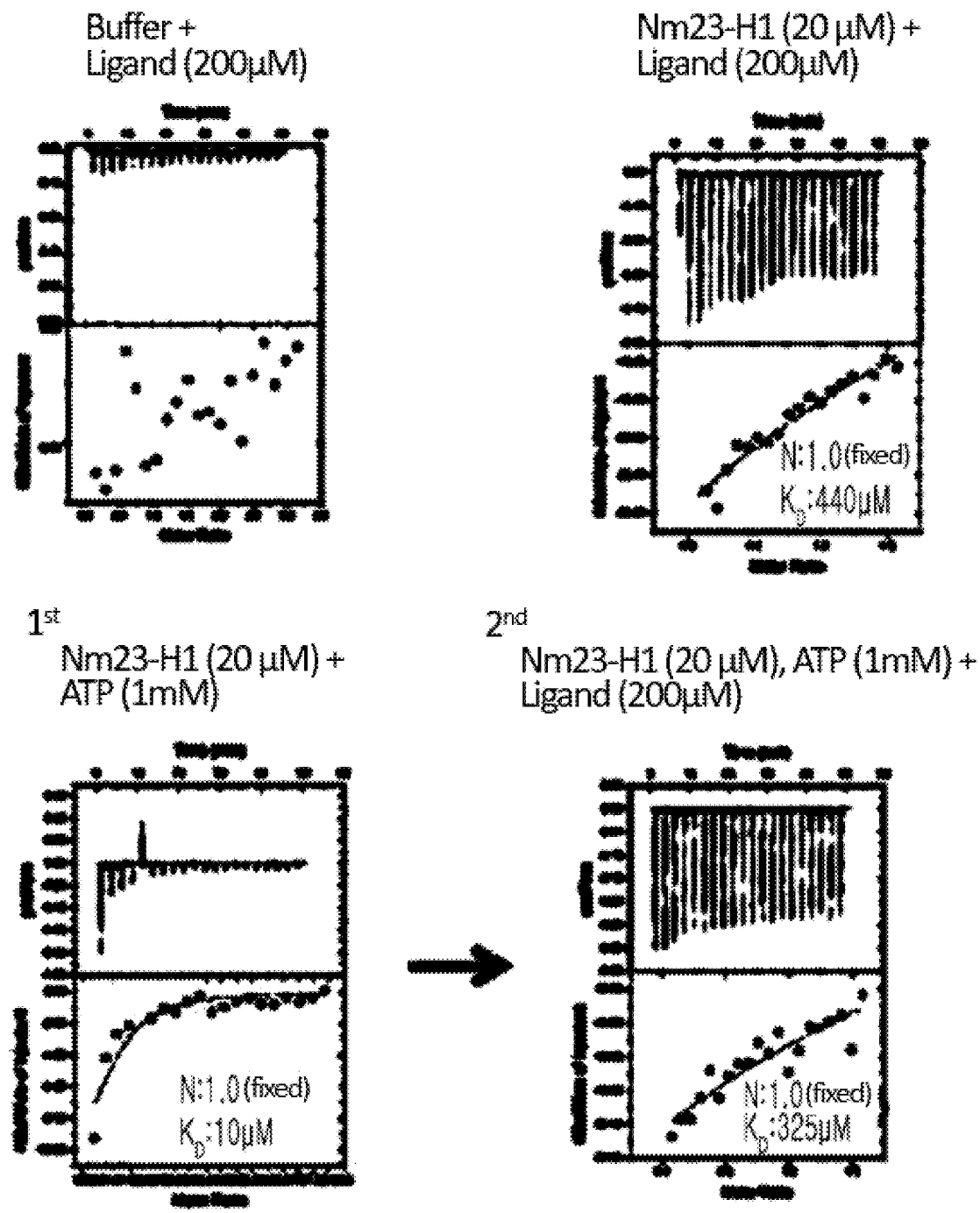
FIG. 4 shows the results of performing isothermal titration calorimetry on a compound of Formula 2-1.

The compound represented by Formula 1 according to the present disclosure, a stereoisomer thereof, or a pharmaceutically acceptable salt thereof may further promote the activity of Nm23 in the presence of ATP (FIG. 4).

In one embodiment of the present disclosure, the cancer may be any one selected from the group consisting of breast cancer, lung cancer, melanoma, prostate cancer, colorectal cancer, bladder cancer, bone cancer, blood cancer, thyroid cancer, parathyroid cancer, bone marrow cancer, rectal cancer, throat cancer, laryngeal cancer, esophageal cancer, pancreatic cancer, gastric cancer, tongue cancer, skin cancer, brain tumor, uterine cancer, head or neck cancer, gallbladder cancer, oral cancer, colon cancer, anal cancer, central nervous system tumor, liver cancer, and colorectal cancer.

In one embodiment of the present disclosure, the pharmaceutical composition of the present disclosure may further contain components, which do not increase the effect of the composition but may be commonly used in pharmaceutical compositions to improve the smell, taste, visual aspect and the like of the compositions. In addition, the pharmaceutical composition of the present disclosure may further contain pharmaceutically acceptable additives. The pharmaceutically acceptable additives include, for example, but are not limited to, starch, gelatinized starch, microcrystalline cellulose, lactose, povidone, colloidal silicon dioxide, calcium hydrogen phosphate, milk sugar, mannitol, malt, gum Arabic, pregelatinized starch, corn starch, powdered cellulose, hydroxypropyl cellulose, Opadry, sodium starch glycolate, carnauba lead, synthetic aluminum silicate, stearic acid, magnesium stearate, aluminum stearate, calcium stearate, white sugar, dextrose, sorbitol and talc.

In addition, the pharmaceutical composition may further contain one or more active ingredients exhibiting the same or similar medicinal effect, in addition to the compound represented by Formula 1, a stereoisomer thereof, or a pharmaceutically acceptable salt thereof.

The pharmaceutical composition of the present disclosure may contain pharmaceutically acceptable carriers and may be formulated for oral or parenteral administration and for human or veterinary use. The pharmaceutical composition of the present disclosure may be formulated using diluents or excipients, including fillers, extenders, binders, wetting agents, disintegrants and surfactants. Solid formulations for oral administration include tablets, pills, powders, granules, capsules and the like, and such solid formulations may be prepared by mixing the pharmaceutical composition containing the compound of the present disclosure with at least one excipient, for example, starch, calcium carbonate, sucrose, lactose, gelatin or the like. In addition to simple excipients, lubricants may be used, such as magnesium stearate and talc. Liquid formulation for oral administration include suspensions, liquid solutions, emulsions and syrups, and may include various excipients, for example, wetting agents, sweeteners, flavoring agents and preservatives, in addition to water and liquid paraffin, which are frequently used simple diluents. Formulations for parenteral administration include sterilized aqueous solutions, non-aqueous solutions, suspensions, emulsions, freeze-dried formulations, and suppositories. As non-aqueous solvents or suspending agents, there may be used propylene glycol, polyethylene glycol, vegetable oils such as olive oil, injectable esters such as ethyl oleate, and the like. As the base of the suppositories, there may be used witepsol, Macrogol, Tween 61, cacao butter, laurin fat, glycerogelatin, and the like.

The pharmaceutical composition of the present disclosure may be administered orally or parenterally according to a desired method. For parenteral administration, the pharmaceutical composition may be applied externally to the skin or administered by intraperitoneal injection, intrarectal injection, subcutaneous injection, intravenous injection, intramuscular injection or intrathoracic injection, but is not limited thereto.

In addition, the pharmaceutical composition of the present disclosure may be used alone, but may also be used in combination with various cancer treatment methods, such as radiotherapy, chemotherapy, etc., in order to increase the efficiency of treatment.

An another aspect of the present disclosure is directed to a method for suppressing cancer metastasis comprising a therapeutically effective amount of a composition containing the compound represented by Formula 1, a stereoisomer thereof, or a pharmaceutically acceptable salt thereof.

A still another aspect of the present disclosure is directed to the use of the compound represented by Formula 1, a stereoisomer thereof, or a pharmaceutically acceptable salt thereof, for the manufacture of a medicament for suppressing cancer metastasis.

The pharmaceutical composition of the present disclosure may be administered to a subject to suppress cancer metastasis. As used herein, the term "subject" refers to mammals such as horses, sheep, pigs, goats, etc., including humans who have a cancer or a disease caused directly or indirectly thereby and in whom symptoms of the disease may be improved by administering the pharmaceutical composition of the present disclosure, but is not limited thereto.

As used herein, the term "administering" means introducing the pharmaceutical composition of the present disclosure to a subject by any suitable method. Regarding the route of administration, the pharmaceutical composition of the present disclosure may be administered orally or parenterally via any route as long as it may reach a target tissue. In addition, the pharmaceutical composition of the present disclosure may be administered by any device that allows the pharmaceutical composition to migrate to target cells.

The pharmaceutical composition of the present disclosure may be administered in a pharmaceutically effective amount. As used herein, the term "pharmaceutically effective amount" refers to an amount sufficient to treat diseases, at a reasonable benefit/risk ratio applicable to any medical treatment. The effective dose level of the pharmaceutical composition may be determined depending on factors, including the patient's body weight, sex, age, health conditions, the severity of the disease, the activity of the drug, sensitivity to the drug, the duration of administration, the route of administration, excretion rate, the duration of treatment, drugs used in combination with the composition, and other factors well known in the medical field. The pharmaceutical composition of the present disclosure may be administered individually or in combination with other therapeutic agents. For co-administration, the pharmaceutical composition may be administered sequentially or simultaneously with conventional therapeutic agents. The pharmaceutical composition may be administered in a single or multiple dosage form. It is important to administer the pharmaceutical composition in the minimum amount that can exhibit the maximum effect without causing side effects, in view of all the above-described factors, and this amount can be easily determined by a person skilled in the art. The pharmaceutical composition may be administered once or several times a day. However, the above-described dose and administration mode are not intended to limit the scope of the present disclosure.

Mode for Disclosure

Hereinafter, the present disclosure will be described in more detail with reference to the following Examples and Test Examples. It is to be understood, however, that the following Examples are not intended to limit the scope of the present disclosure and are provided to aid the understanding of the present disclosure.

Preparation Example 1. Compound of Formula 2-1

(1) Process A

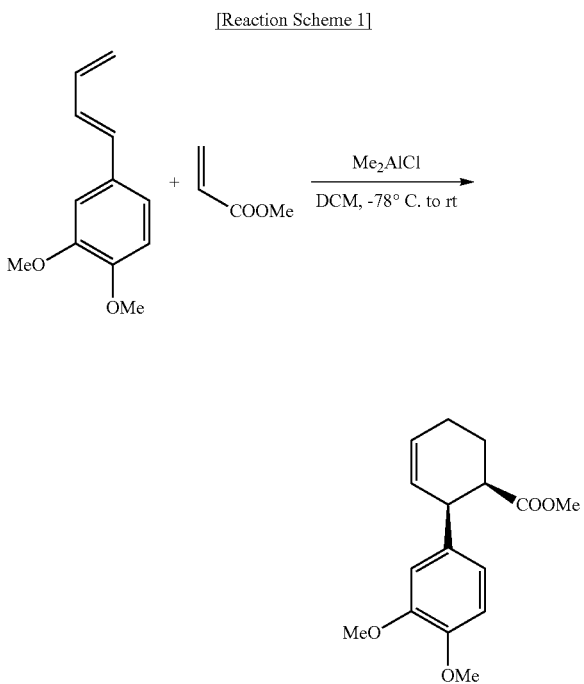

[Reaction Scheme 1]

(E)-4-(buta-1,3-dienyl)-1,2-dimethoxybenzene (1.0 equivalent) and methyl acrylate (1.5 equivalents) were dissolved in dichloromethane, and then $Me_2AlCl$ (1.0 M in hexane) (1.1 equivalents) was added slowly thereto at −78° C. The mixture was warmed to room temperature, and then stirred overnight. Then, the temperature was lowered again to 0° C., and the reaction was terminated by adding ammonium chloride and distilled water to the mixture, followed by extraction with dichloromethane. The extracted organic layer was dried with $MgSO_4$, and then filtered and concentrated. The mixture was separated on silica gel by column chromatography.

(2) Process B

[Reaction Scheme 2]

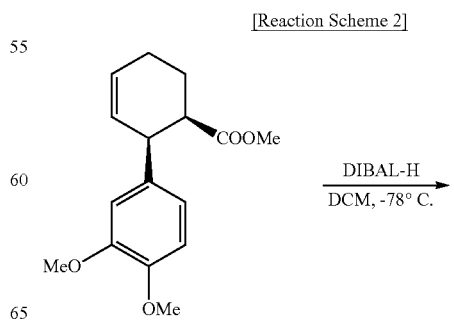

(3) Process C

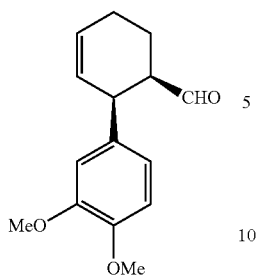

At −78° C., DIBAL-H (1.0 M in DCM, 1.05 equivalents) was added slowly to a solution of (1R,2S) methyl 2-(3,4-dimethoxyphenyl)cyclohex-3-enecarboxylate (1.0 equivalent). The mixture was stirred at −78° C. for 2 hours, distilled water (10 equivalents) and NaF (5.0 equivalents) were added thereto, followed by stirring at room temperature for 30 minutes. The mixture was filtered through silica and Celite, and then concentrated and separated on silica gel by column chromatography.

(3) Process C

[Reaction Scheme 3]

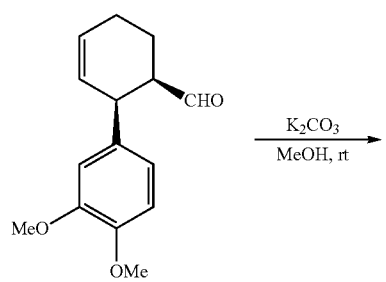

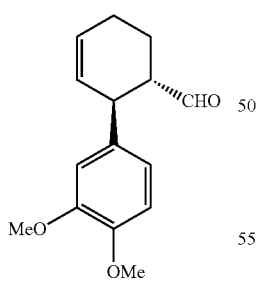

K₂CO₃ was added to a solution of (1R,2S)-2-(3,4-dimethoxyphenyl)cyclohex-3-enecarbaldehyde (1.0 equivalent) in methanol at room temperature. The mixture was subjected to an epimerization reaction for about 36 to 72 hours, and then diluted with ethyl acetate, and the reaction was terminated by adding ammonium chloride and water. The reaction mixture was extracted with ethyl acetate, and then concentrated and separated on silica gel by column chromatography.

(4) Process D

[Reaction Scheme 4]

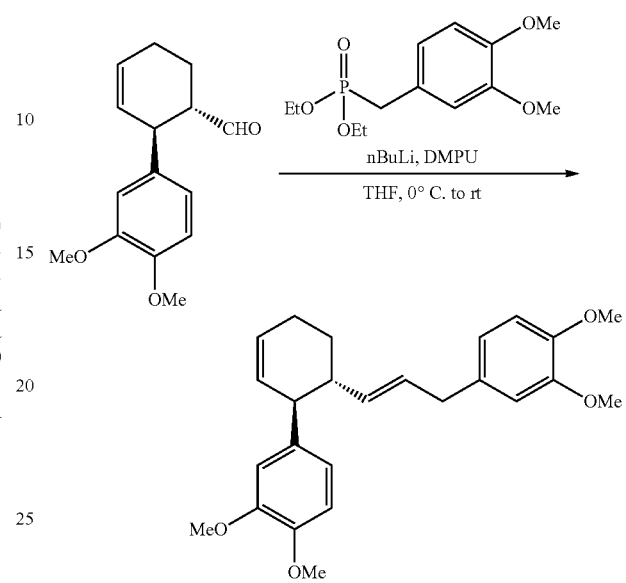

nBuLi (2.48 M in hexane) (1.95 equivalents) was added to a solution of diethyl 3,4-dimethoxybenzyl phosphonate (2.0 equivalents) in tetrahydrofuran at 0° C. The mixture was stirred at mom temperature for 30 minutes, and then the temperature was lowered again to 0° C., and a solution of (1S,2S)-2-(3,4-dimethoxyphenyl)cyclohex-3-enecarbaldehyde (1.0 equivalent) and DMPU (5.0 equivalents) in THF was added to the mixture through a cannula. The mixture was stirred overnight at mom temperature, and then the reaction was terminated by adding ammonium chloride and water. The reaction mixture was extracted with ethyl acetate, dried with MgSO₄, and then concentrated and separated on silica gel by column chromatography.

The results of ¹H NMR of the produced compound of Formula 2-1 are as follows.

[Formula 2-1]

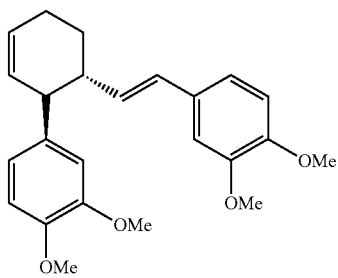

$^1$H NMR (599 MHz, CDCl$_3$) δ6.81-6.75 (m, 2H), 6.78-6.72 (m, 2H), 6.71 (dd, J=8.2, 1.8 Hz, 1H), 6.68 (d, J=1.8 Hz, 1H), 6.07 (d, J=15.9 Hz, 1H), 6.00 (dd, J=15.9, 7.4 Hz, 1H), 5.88 (ddt, J=9.6, 4.9, 2.8 Hz, 1H), 5.66 (dd, J=10.0, 2.1 Hz, 1H), 3.85 (s, 3H), 3.84 (s, 3H), 3.83 (s, 3H), 3.80 (s, 3H), 3.16 (dt, J=8.2, 2.6 Hz, 1H), 2.33 (dtd, J=10.7, 7.7, 2.8 Hz, 1H), 2.20 (ddp, J=6.5, 4.5, 2.4 Hz, 2H), 1.90 (dq, J=12.3, 4.5 Hz, 1H), 1.65 (dtd, J=12.9, 10.1, 6.2 Hz, 1H).

(5) Mass Synthesis Process

The compound of Formula 2-1 may also be produced according to the following Reaction Formula 5:

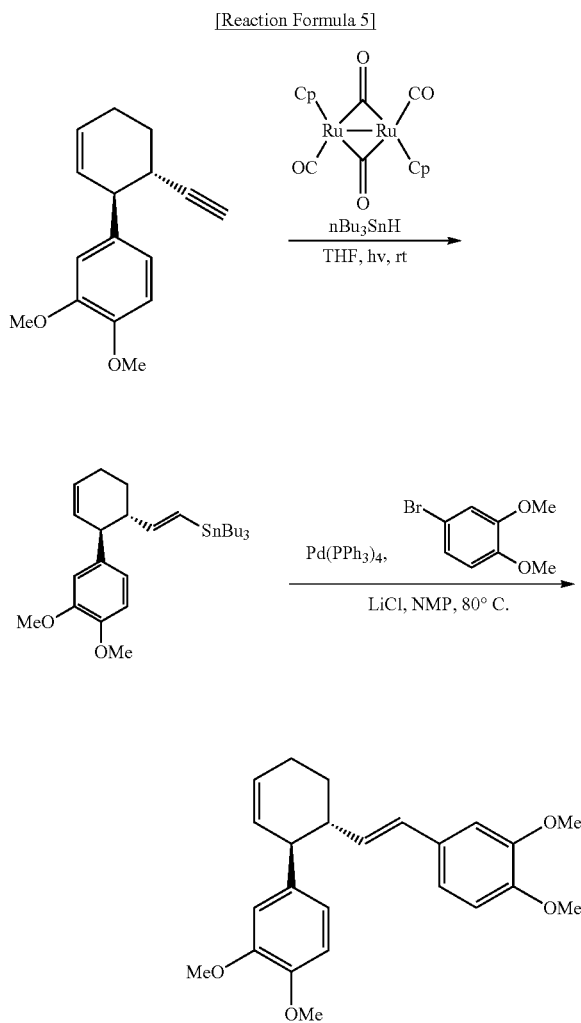

4-((1S,6S)-6-ethynylcyclohex-2-enyl)-1,2-dimethoxybenzene (1.0 equivalent) (which may be synthesized using the method described in J. Chu et al., *J. Nat. Prod.* 2011, 74, 1817) was dissolved, and then a ruthenium catalyst (0.1 equivalents) was added thereto at room temperature. The mixture was degassed for 15 minutes, and then tributyltin hydride (2.0 equivalents) was added thereto. The mixture was stirred under LED light for 2 hours, and then the solvent was evaporated under vacuum. The remaining mixture was filtered through a thin silica pad, concentrated under vacuum, and then immediately used in the next reaction.

Vinyl stannane (1.0 equivalent) was dissolved in NMP, and then 4-bromo-1,2-dimethoxybenzene (1.2 equivalents), LiCl (1.2 equivalents) and Pd(PPh$_3$)$_4$ were added thereto and stirred at room temperature. After 5 hours, the mixture was washed with ethyl acetate, and then washed with brine. The extracted organic layer was dried with MgSO$_4$, filtered, concentrated, and then separated on silica gel by column chromatography.

Preparation Example 2. Compound of Formula 3-1

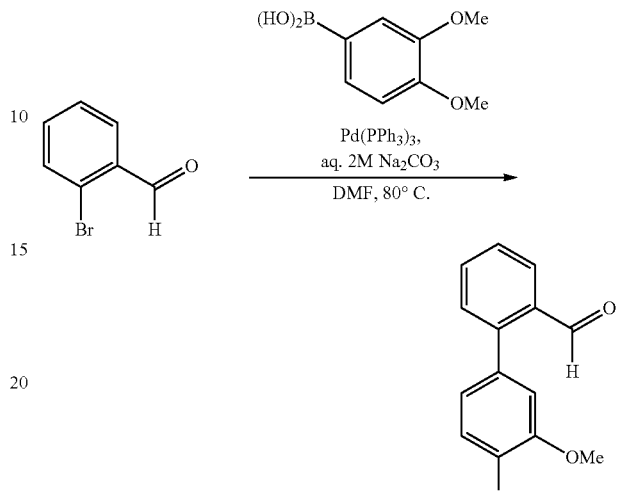

o-bromobenzaldehyde (1.0 equivalent) was dissolved in DMF, and then 3,4-dimethoxyphenylboronic acid (1.0 equivalent), 2M Na$_2$CO$_3$ (3.0 equivalents) and Pd(PPh$_3$)$_4$ (0.01 equivalents) were added thereto at mom temperature. The mixture was stirred overnight at 80° C. and diluted with ethyl acetate, and then the reaction was terminated by adding ammonium chloride and water. Thereafter, the mixture was extracted with ethyl acetate, and the organic layer was dried with MgSO$_4$. The mixture was filtered, and the collected organic layer was concentrated, and then separated on silica gel by column chromatography.

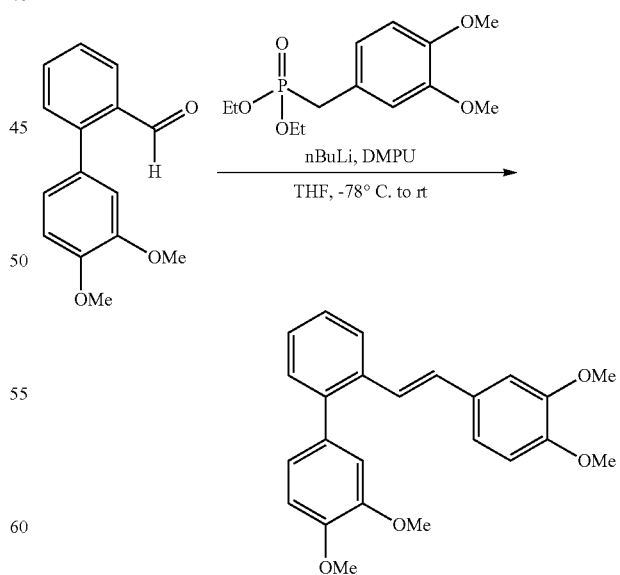

The compound d of Formula 3-1 was synthesized in the same manner as process D of Preparation Example 1 above. The results of $^1$H NMR of the produced compound of Formula 3-1 are as follows.

[Formula 3-1]

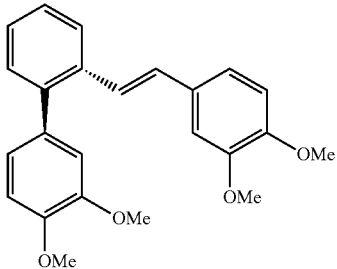

¹H NMR (599 MHz, CDCl3) δ7.70 (d, J=7.6 Hz, 1H), 7.33 (d, J=7.1 Hz, 2H), 7.30 (d, J=6.2 Hz, 1H), 7.03-6.91 (m, 6H), 6.89 (d, J=1.6 Hz, 1H), 6.80 (d, J=8.3 Hz, 1H), 3.92 (s, 3H), 3.86 (s, 3H), 3.84 (s, 3H), 3.83 (s, 3H).

Preparation Example 3. Compound of Formula 4-1

[Reaction Scheme 8]

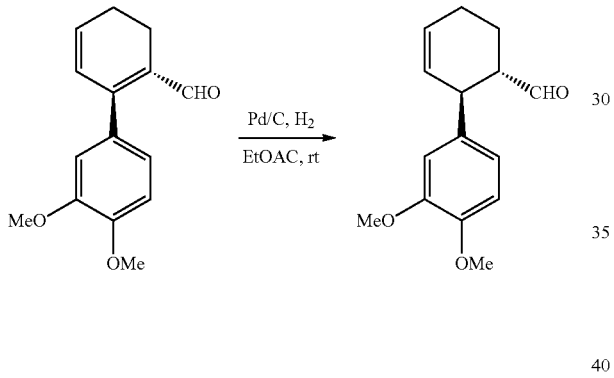

The (1S,2S)-2-(3,4-dimethoxyphenyl)cyclohex-3-enecarbaldehyde (1.0 equivalent) produced according to processes A to C of Preparation Example 1 above was dissolved in ethyl acetate, and then 10 wt % (0.1 equivalents) of Pd/C was added thereto at room temperature. After 6 hours, the mixture was filtered through silica and Celite, and then washed with ethyl acetate. Next, the collected organic mixture was concentrated, and then separated on silica gel by column chromatography.

[Reaction Scheme 9]

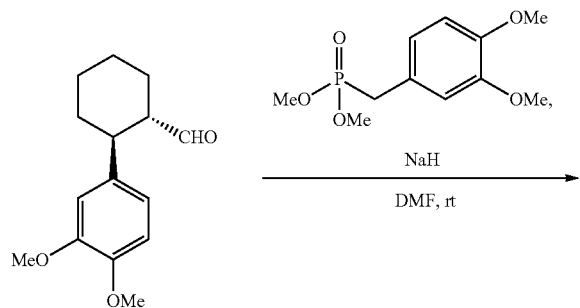

-continued

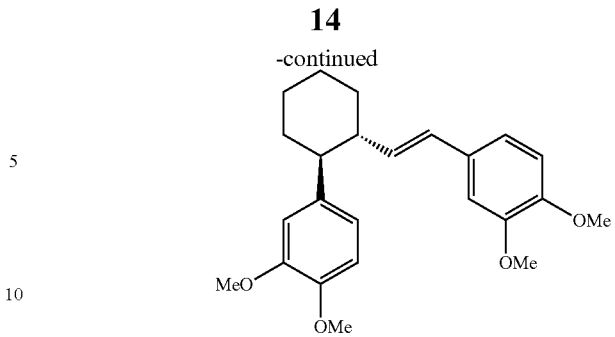

Dimethyl(3,4-dimethoxybenzyl)phosphonate (2.0 equivalents) was dissolved in DMF, and then NaH (60% in mineral oil) (1.95 equivalents) was added thereto at 0° C. Thereafter, the mixture was stirred at room temperature for 30 minutes, and then a solution of (1S,2S)-2-(3,4-dimethoxyphenyl)cyclohexanecarbaldehyde (1.0 equivalent) in DMF was added thereto through a cannula. The mixture was stirred overnight at room temperature, and then the reaction was terminated by adding ammonium chloride and water. Thereafter, the reaction mixture was extracted with ethyl acetate, and then dried with $MgSO_4$. The dried mixture was filtered, and then the organic layer was concentrated and separated on silica gel by column chromatography. The results of ¹H NMR of the produced compound of Formula 4-1 are as follows.

[Formula 4-1]

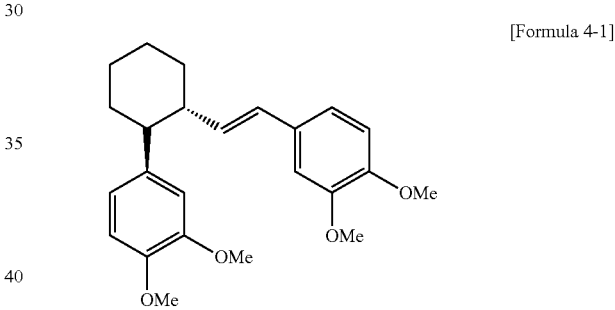

¹H NMR (400 MHz, Chloroform-d) δ7.07-6.98 (m, 4H), 6.91 (s, 2H), 6.84 (d, J=8.2 Hz, 2H), 6.74 (d, J=8.0 Hz, 1H), 6.72-6.65 (m, 5H), 6.04 (d, J=15.9 Hz, 1H), 5.77 (dd, J=15.9, 6.9 Hz, 1H), 3.93 (s, 6H), 3.88 (s, 6H), 3.82 (s, 3H), 3.81 (s, 9H), 2.35-2.21 (m, 2H), 1.87 (td, J=19.9, 16.5, 9.8 Hz, 5H), 1.38 (t, J=10.8 Hz, 9H).

Example 1. Analysis of NDPK Activity (1) NDPK Assay 5 ng of recombinant Nm23-H1 was incubated with 5 µM ADP and a test substance (the compound of Formula 2-1, 3-1 or 4-1) in NDPK assay buffer (20 mM HEPES, 3 mM $MgCl_2$) at mom temperature for 1 minute, and cell-based NDPK assay was performed. A cell lysate obtained from 5,000K MDA-MB-231 cells lysed with a protease inhibitor cocktail and an NDPK assay buffer was centrifuged at 8,000 rpm for 10 minutes at 4° C. 40 µL of the lysate was incubated with the test substance for 5 minutes, and then 50 µM UDP was added thereto and reacted with NDPK. ATP consumption was assessed by an ATP determination kit (Molecular probe, USA).

(2) Isothermal Titration Calorimetry

An ITC experiment was performed using the ITC200 system (Malvern Inc.), and the data were analyzed using ORIGIN 7.0 program. The concentration of Nm23-H1 protein in the cells was 30 μM, and the syringe contained 300 μM of the activator or 1 mM ATP. The activator was prepared at a concentration of 50 mM in DMSO (dimethyl sulfoxide) and stored at −20° C. ITC buffer contained (pH 7.5) 150 mM NaCl, 3 mM $MgCl_2$ and 20 mM HEPES in up to 2% DMSO. For titration, each 2 μL was injected 20 times 25° C. at intervals of 150 seconds. No evidence of DMSO binding at the nucleotide binding site was observed. The experimental raw data were corrected by subtracting the value for the buffer, and then fitted to a single site binding model. The titration data were fitted using a nonlinear least squares curve-fitting algorithm with three floating variables: stoichiometry (N), dissociation constant (KD), and change of enthalpy of interaction.

(3) Surface Plasmon Resonance Analysis

The interaction between the compound of Formula 2-1 and Nm23-H1 was analyzed using a surface plasmon resonance instrument (SR7500 DC, Reichert Inc., NY) at 25° C.

Nm23-H1 (1 mg/ml) in 10 mM S.A buffer (pH 4.5) was immobilized using the standard amino coupling at 20 μL/min for 10 minutes on a carboxymethyl dextran hydrogel (CMDH) surface sensor chip (Reichert Technologies, NY) until saturation was achieved.

Different concentrations of the compound of Formula 2-1 (10-160 μM) in binding buffer (10 mM HEPES, pH 7.4, 100 mM NaCl, 1 mM $MgCl_2$, and with or without 2 mM ATP) were allowed to flow over the immobilized Nm23-H1 (approximately 8200 RU) at a rate of 30 μL/min.

The sensor surface was regenerated after each association and dissociation cycle by injecting 2M NaCl for 1 min. Sensorgrams were fitted to a simple 1:1 Langmuir interaction model (A+B⇌AB) using data analysis program Scrubber 2.0 (BioLogic Sofware, Australia, and Kaleida Graph Sofware, Australia).

The values obtained by averaging at least three independent runs of SPR measurements are shown in Table 1 below. $K_D$ is a value obtained by calculating $K_d/K_a$.

TABLE 1

| Ligand | $Ka^\alpha[M^{-1} S^{-1}]$ | $Kd^\alpha[S^{-1}]$ | $K_D^b[M]$ |
|---|---|---|---|
| Formula 2-1 | 78 ± 1 | $1.39 \pm 0.01^{-3}$ | 17.9 ± 0.2 μM |
| Formula 2-1, 2 nM ATP | 71 ± 1 | $1.06 \pm 0.07e^{-4}$ | 1.49 ± 0.03 μM |

Looking at the results in Table 1 above, it can be seen that in the presence of ATP, the dissociation is slowed and the $K_D$ value decreases. From these results, it can be confirmed that the interaction between Nm23-H1 and the compound of the present disclosure is further enhanced in the presence of ATP.

FIG. 3 shows the results of analyzing the activity of NDPK for the compound of Formula 2-1. Hereinafter, the compound of Formula 2-1 in each figure was indicated as NMac1.

Specifically, from the results in FIG. 3A, it can be seen that the NDPK activity of Nm23-H1 increased depending on the concentration of the compound of Formula 2-1. As shown in FIG. 3B, the V0, Km value of the enzyme was measured by measuring the activity of NDPK depending on the concentration of UDP, and as a result, it could be confirmed that the compound showed Km-type activity similar to that of a conventional enzyme activator. From this result, it can be seen that the NDPK activator increases the activity of NDPK by increasing the affinity for the substrate NTP. In addition, from the results in FIG. 3C, it was confirmed that the cell-based NDPK activity increased depending on the concentration of the compound of Formula 2-1. In addition, as shown in FIG. 3D, it could be confirmed that the compound of Formula 2-1 according to the present disclosure showed the same activity not only for Nm23-H1, but also for Nm23-H2 which is another subtype of Nm23. More specifically, it can be confirmed through FIG. 3E that the compound of Formula 2-1 according to the present disclosure specifically activates only Nm23-H1 which is the active form of Nm23-H1.

In addition, compounds of Formulas 3-1 and 4-1 as derivatives of the compound of Formula 2-1 were produced, and the NDPK activities of the derivatives were analyzed. The relative NDPK activity of each test substance relative to a DMSO-treated group is shown in Table 2 below.

TABLE 2

| Formula | Compound | Relative NDPK activity (±S.D) |
|---|---|---|
| — | DMSO | 1 |
| 2-1 | (cyclohexene-substituted stilbene with four OMe groups) | 4.04 (±0.13) |
| 3-1 | (benzene-substituted stilbene with four OMe groups) | 4.11 (±0.16) |
| 4-1 | (cyclohexane-substituted stilbene with four OMe groups) | 2.41 (±0.29) |

From the above results, it was confirmed that the compounds corresponding to Formula 1, that is, the compound of Formula 2-1 and its derivatives (the compounds of Formulas 3-1 and 4-1), all have excellent NDPK activity (increased activity on Nm23). Thus, additional experiments on the Nm23 activity of the compound of Formula 2-1 were subsequently performed.

FIG. 4 shows the results of performing isothermal titration calorimetry for the compound of Formula 2-1. From the results in FIG. 4, it could be confirmed that the direct interaction between Nm23-H1 and the compound of Formula 2-1 according to the present disclosure occurred and was further enhanced in the presence of ATP.

Figure 5:
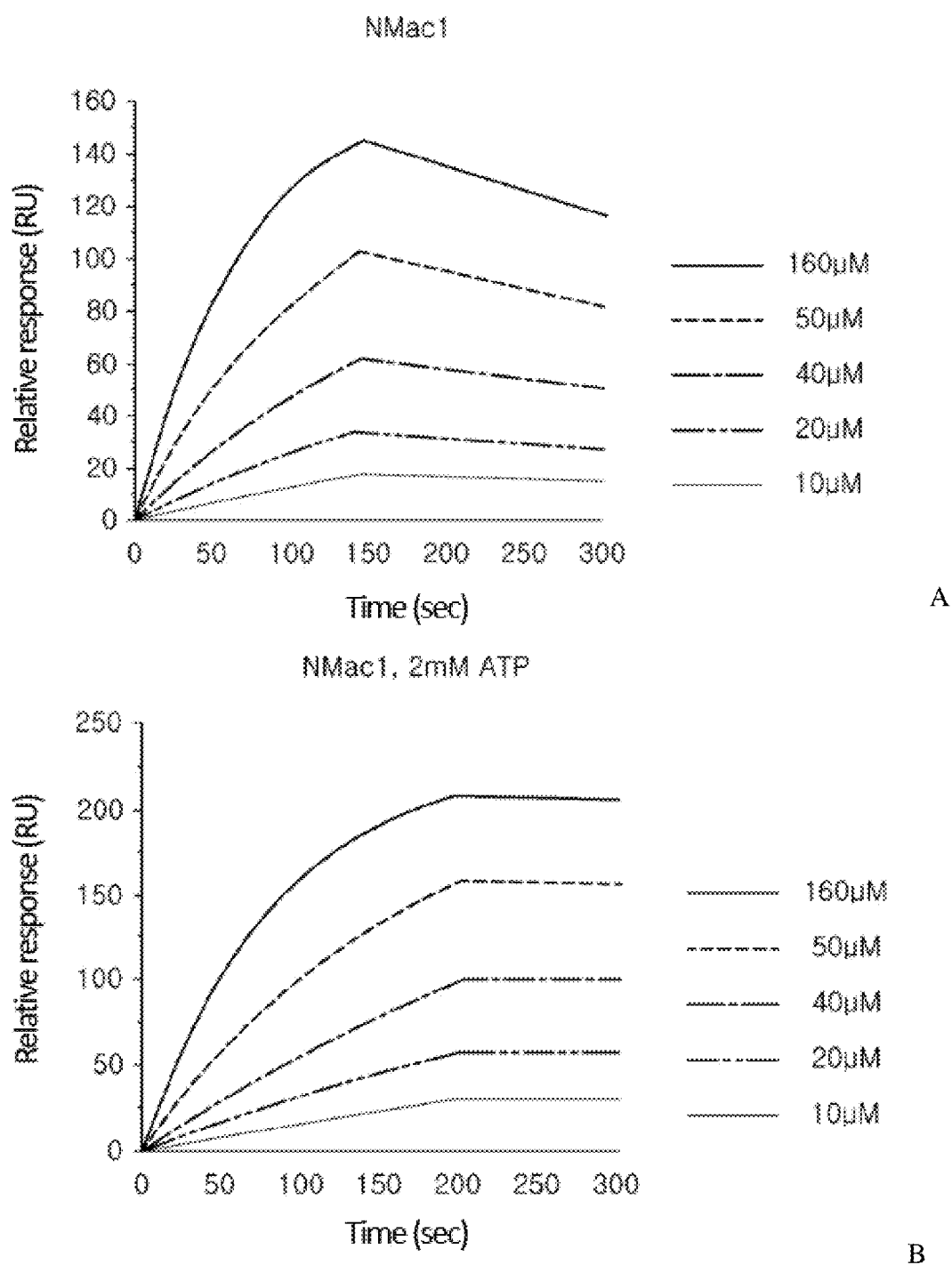
FIG. 5 panels A-B show the results of plasmon resonance analysis.

FIG. 5 shows the results of plasmon resonance analysis. From the results in FIG. 5, it could be confirmed that the compound of the present disclosure did bind directly to Nm23-H1.

Example 2. Verification of Metastasis Suppressing Activity of the Compound of Formula 2-1

(1) Rac1 Activity Assay

MDA-MB-231 cells were grown in a 100 mm dish and treated with the compound of Formula 2-1 or 0.05% DMSO at an indicated concentration for 16 hours. Active Rac1 pulldown assays were performed according to the manufacturer's instructions (Termo Fisher Scientifc).

(2) Immunofluorescence Analysis

MDA-MB-231 cells were grown on the Secureslip™ (Sigma) cell culture glass cover slip to a confluence of 50 to 70%, and incubated in the presence or absence of the compound of Formula 2-1 for various periods of time. The cells were gently washed with cold HBSS, and then fixed with 4% paraformaldehyde-containing HBSS in RBS for 10 minutes. After washing with HBSS, permeabilization with 0.1% Triton X-100 was performed for 10 minutes at mom temperature. After washing twice with HBSS, the cells were blocked with HBSS containing 3% BSA, 0.2% Tween 20 and 0.2% gelatin at room temperature for 1 hour, and incubated with primary antibody at mom temperature for 1 hour. Then, the cells were incubated with fluorochrome-conjugated species-specific secondary antibodies for 1 hour.

All the antibodies were diluted with 1% BSA-containing HBSS. Coverslips were mounted with anti-fading solution, and viewed using a ×63 objective lens of an LSM510 META (Zeiss) laser scanning confocal microscope.

(3) Invasion Assay

When cells reached a confluence of 70%, the cells were treated with the compound of Formula 2-1 for 16 hours. $1 \times 10^5$ cells were suspended in PBS-free medium and added onto a Boyden chamber membrane. 10% PBS-containing culture was added to the bottom of the membrane. The chamber was incubated at 37° C. under 5% $CO_2$ for 4 hours. The migrated cells were fixed and stained with crystal violet/methanol. The cells were photographed, and the migrated cells were counted and normalized to control cells.

FIG. 6 shows the results obtained by two types of breast cancer cell lines with the compound of Formula 2-1, observing the morphological changes of the cells and observing the Rac1 activity in each of the cell lines.

FIG. 6A shows the confocal microscopic observation of the cells treated with the compound of Formula 2-1. Looking at the change of F-actin in the MDA-MB-231 cells, it can be confirmed that ruffles decreased and intercellular contact increased. This implies that Nm23-H1 inhibits the activity of Rac1 involved in cell migration and reduces cell migration.

In addition, FIG. 6B shows the results of measuring changes in morphology and Rac1 activity by treatment with the compound of Formula 2-1 in MDA-MB-231 cells which are a triple negative breast cancer cell line. Referring to FIG. 6B, it can be seen that a pull-down assay of activated Rac1 was conducted, the component of Formula 2-1 according to the present disclosure reduced the activity of Rac1 in a concentration-dependent manner. As shown in FIGS. 6C and 6D, it can be confirmed that the effect of the compound of Formula 2-1 was abolished by knockdown of Nm23-H1. This suggests that inhibition of Rac1 activity occurs through Nm23-H1.

Figure 7:
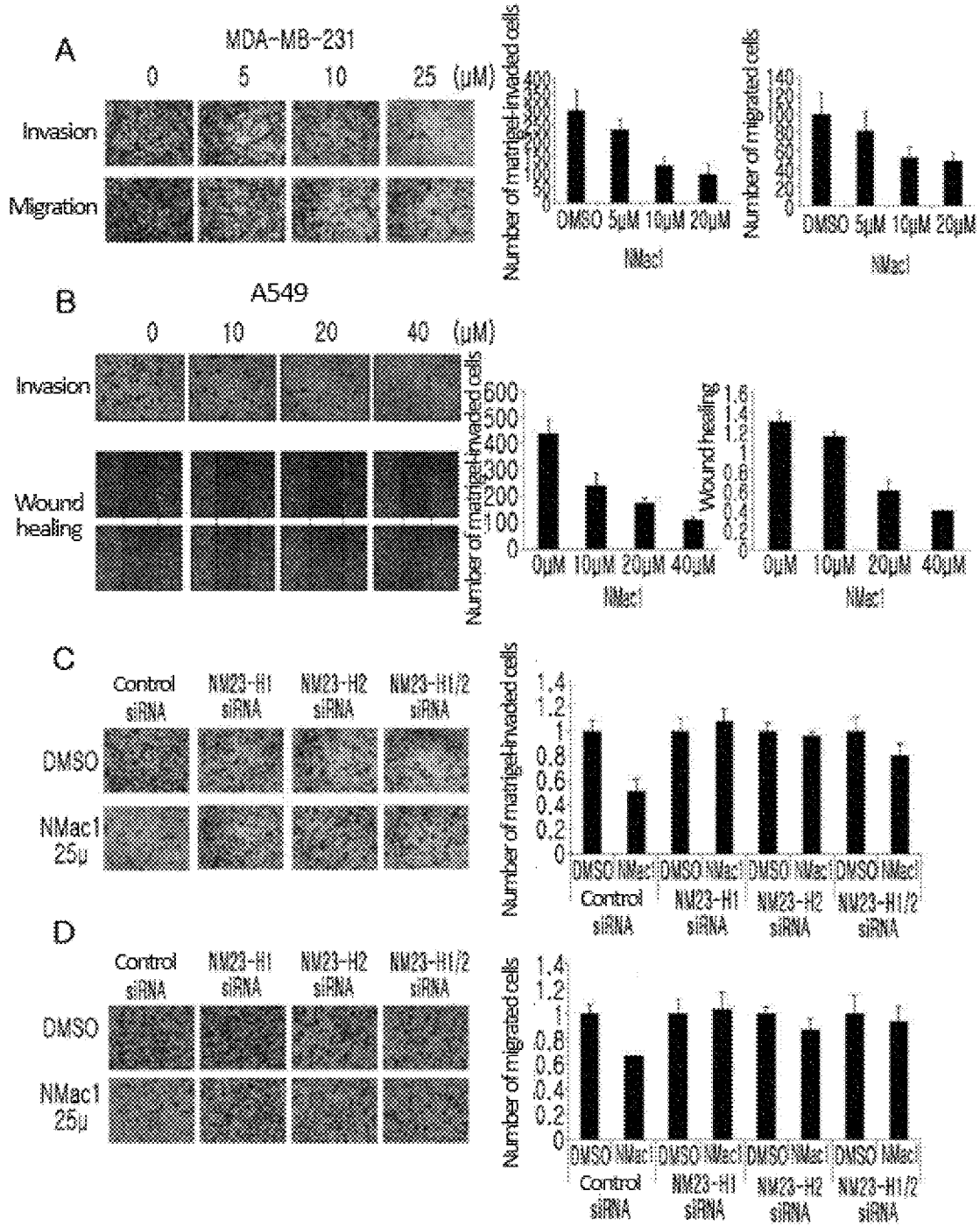
FIG. 7 panels A-D show the results of verifying the invasion and migration inhibitory activity of a compound of Formula 2-1 on MDA-MB-231 cells.

FIG. 7 shows the results of verifying the invasion and migration inhibitory activity of the compound of Formula 2-1 on MDA-MB-231 cells.

FIG. 7A shows the results of performing invasion assay and transwell migration assay in MDA-MB-231 cells which are a triple negative breast cancer cell line.

Referring to FIG. 7A, it can be seen that when MDA-MB-231 cells were treated with different concentrations of the compound of Formula 2-1, the compound of Formula 2-1 reduced transwell migration and matrigel invasion in a concentration-dependent manner.

FIG. 7B shows the Nm23-H1 activity of the compound of Formula 2-1 on A549 cells which are a lung cancer cell line. From the results in FIG. 7B, it can be seen that the compound of Formula 2-1 reduced both the transwell migration and matrigel invasion of A549 cells.

FIG. 7C shows the Nm23-H1 and Nm23-H2 activities of the compound of Formula 2-1. As shown in FIG. 7C, the effect of the compound of Formula 2-1 was reduced by knockdown of Nm23-H1 and Nm23-H2. This suggests that the in vitro metastasis suppressing activity of the compound of Formula 2-1 occurs through Nm23-H1 and Nm23-H2.

Example 3. Verification of Metastasis Suppressing Activity of the Compound of Formula 2-1 Using Breast Cancer Metastasis Model In order to confirm the metastasis suppressing activity of the compound of Formula 2-1 according to the present disclosure in an actual animal model, MDA-MB-231 luc cells were applied to a breast cancer metastasis model. MDA-MB-231 cells were injected into the mammary fat pad of nude mice, and then when the tumor size reached 100 mm, the compound of Formula 2-1 was injected daily at a dose of 10 mg/kg, and the metastasis of the cells to the lung was observed for 4 weeks.

Figure 8:
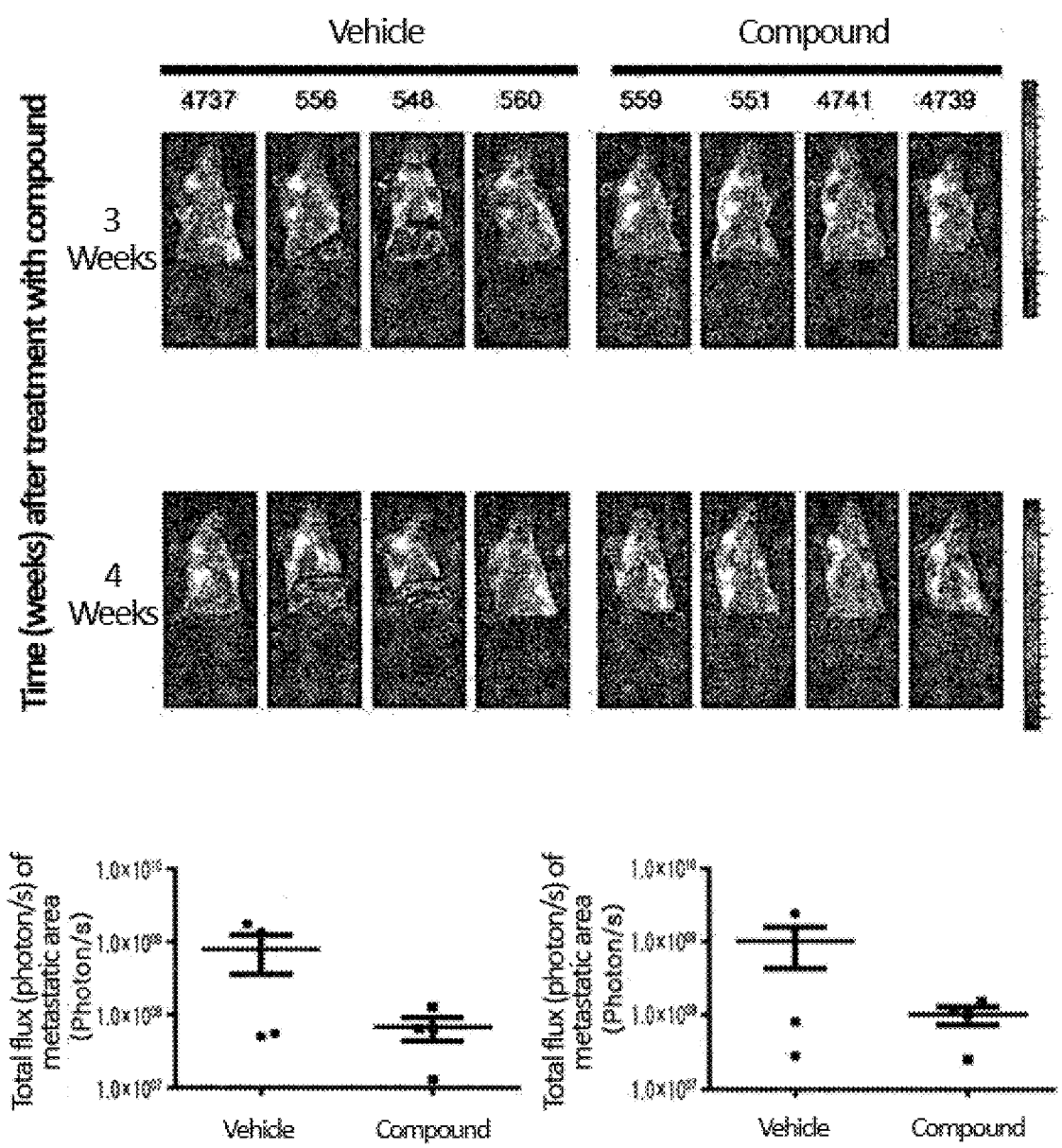
FIG. 8 shows the metastasis suppressing activity of a compound of Formula 2-1 in a breast cancer metastasis model.

FIG. 8 shows the metastasis suppressing activity of the compound of Formula 2-1 in the breast cancer metastasis model. From the results in FIG. 8, it can be seen that metastasis of the cells to the lung decreased in the group treated with the compound of Formula 2-1 according to the present disclosure.

Figure 9:
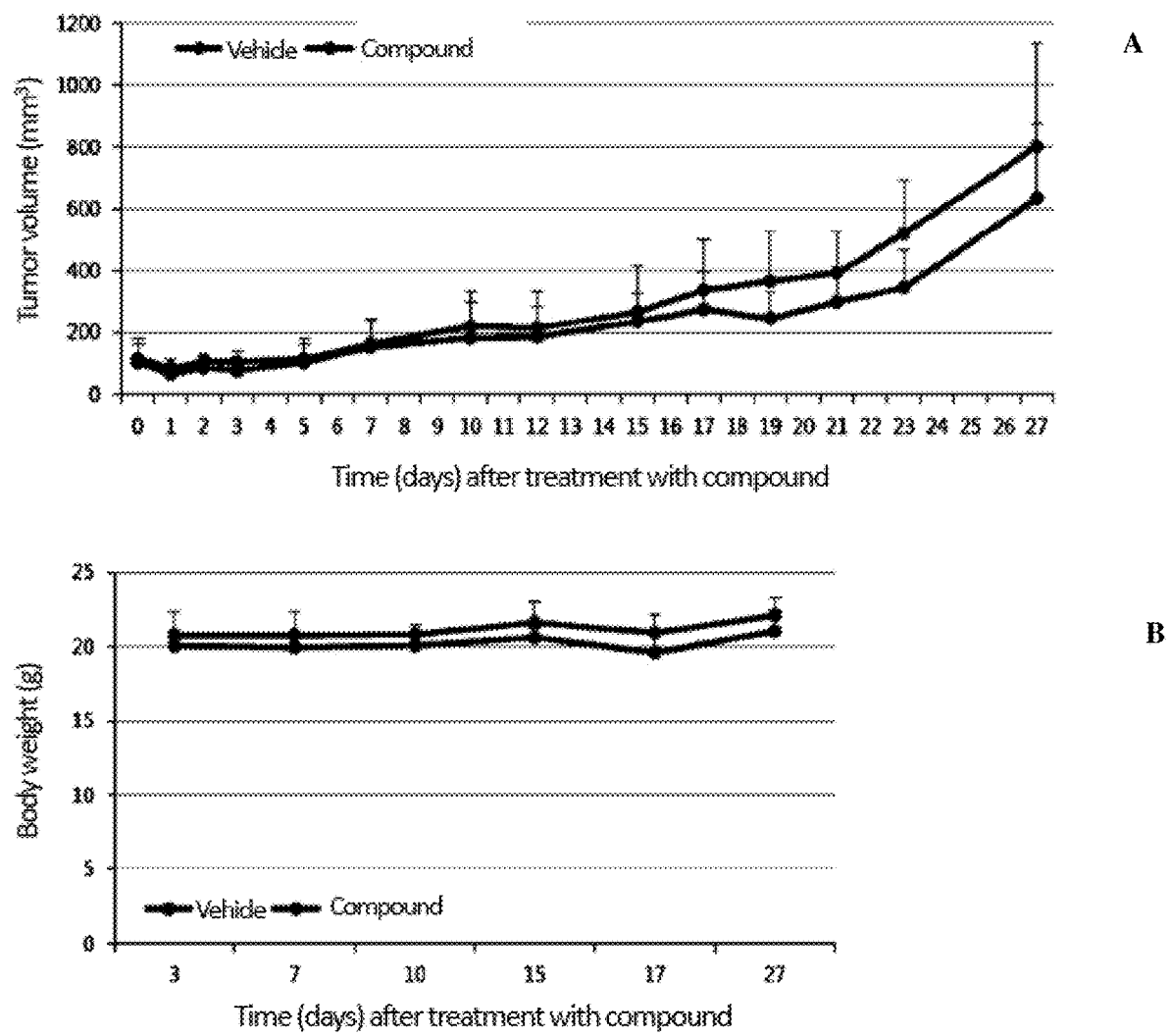
FIG. 9 panels A-B show the changes in tumor volume and mouse body weight by treatment with a compound of Formula 2-1.

FIG. 9 shows the changes in tumor volume and body weight by treatment with the compound of Formula 2-1. From the results in FIG. 9, it could be confirmed that the volume of the tumor decreased in the group treated with the compound of Formula 2-1 according to the present disclosure.

Figure 10:
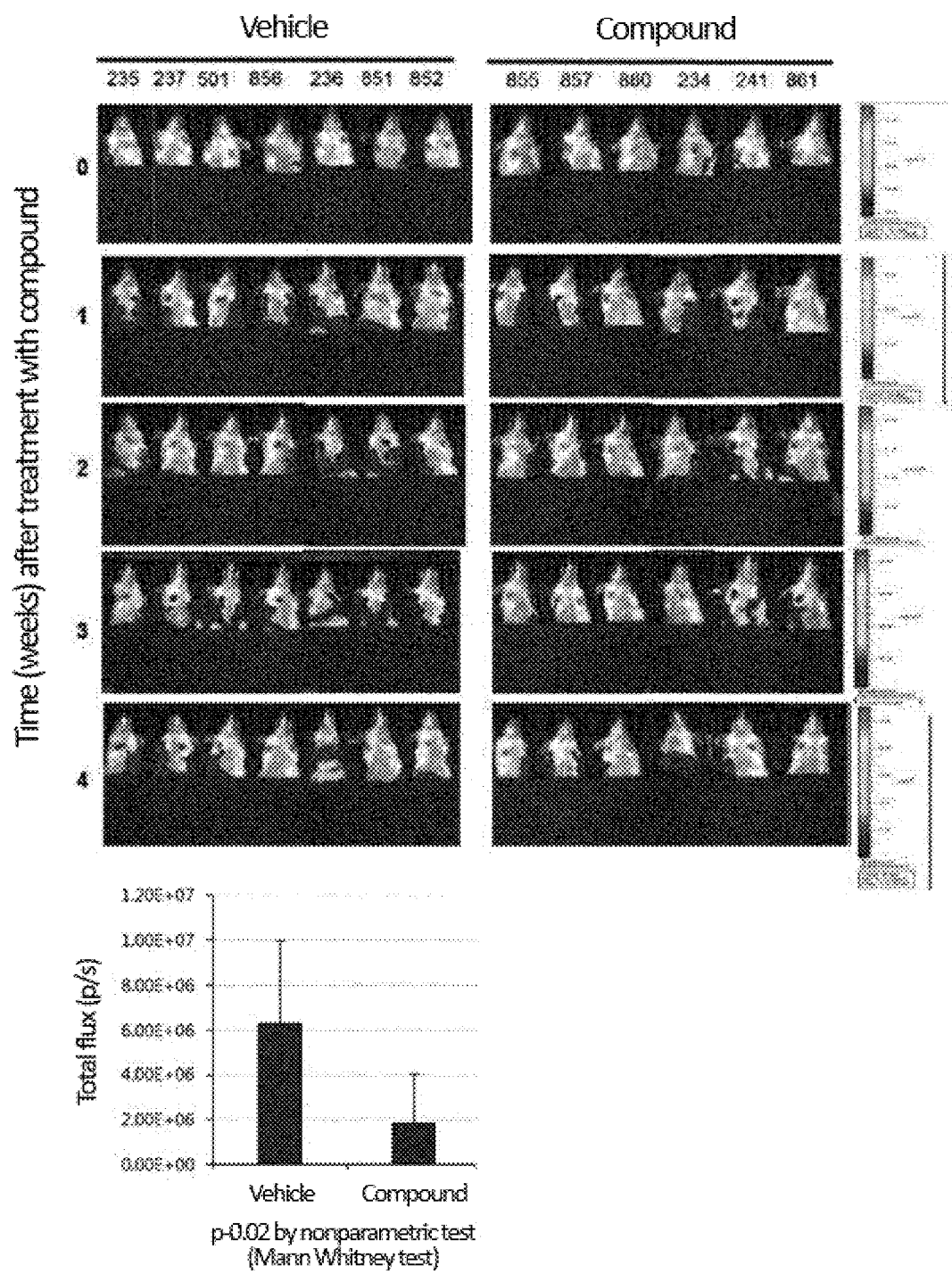
FIG. 10 shows the metastasis suppressing activity of a compound of Formula 2-1 in a breast cancer metastasis model.

FIG. 10 shows the metastasis suppressing activity of the compound of Formula 2-1 in the breast cancer metastasis model. From the results in FIG. 10, it could be confirmed that the cells that metastasized to the lung statistically significantly decreased.

From the results of the Examples above, it can be confirmed that the compound represented by Formula 1 according to the present disclosure may be used as a pharmaceutical composition which is effective for suppressing cancer metastasis by increasing the NDPK activity of Nm23.

In the present specification, the detailed description of contents that can be sufficiently recognized and inferred by those skilled in the technical field to which the present disclosure pertains. In addition, the present disclosure is not limited to the specific embodiments described in the present specification, and various modifications may be made without departing from the spirit or essential features of the present disclosure. Accordingly, those skilled in the technical field to which the present disclosure pertains will appreciate that the present disclosure may be carried out in other ways than those specifically described and illustrated herein.

The invention claimed is:

1. A method for preventing or suppressing cancer metastasis, comprising administering to a subject in need thereof a compound represented by Formula 1, a stereoisomer thereof, or a pharmaceutically acceptable salt thereof as an active ingredient:

[Formula 1]

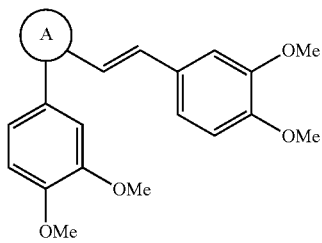

wherein ring A is cyclohexane or benzene.

2. The method of claim 1, wherein the compound represented by Formula 1 is represented by any one of the following Formulas 3 to 4:

[Formula 3]

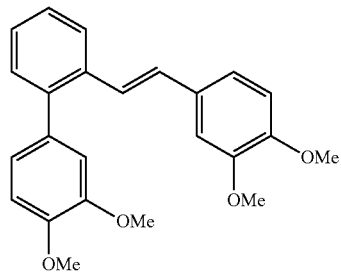

[Formula 4]

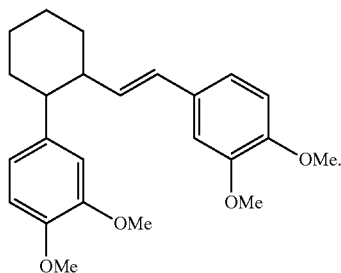

3. The method of claim 1, wherein the compound represented by Formula 1 is an activator of Nm23-H1, an activator of Nm23-H2, or an activator of Nm23-H1 and Nm23-H2.

4. The method of claim 1, wherein the cancer is any one selected from the group consisting of breast cancer, lung cancer, melanoma, prostate cancer, colorectal cancer, bladder cancer, bone cancer, blood cancer, thyroid cancer, parathyroid cancer, bone marrow cancer, rectal cancer, throat cancer, laryngeal cancer, esophageal cancer, pancreatic cancer, gastric cancer, tongue cancer, skin cancer, brain tumor, uterine cancer, head or neck cancer, gallbladder cancer, oral cancer, colon cancer, anal cancer, central nervous system tumor, liver cancer, and colorectal cancer.

* * * * *

UNITED STATES PATENT AND TRADEMARK OFFICE
CERTIFICATE OF CORRECTION

| | |
|---|---|
| PATENT NO. | : 11,389,411 B2 |
| APPLICATION NO. | : 16/609094 |
| DATED | : July 19, 2022 |
| INVENTOR(S) | : Kong Joo Lee et al. |

It is certified that error appears in the above-identified patent and that said Letters Patent is hereby corrected as shown below:

On the Title Page

Item (56) Non-patent literature entitled Shuya Yano et al., "Invading Cancer Cells are Predominantly in G0/G1 Resulting in Chemoresistance Demonstrated by Real-Time FUCCI Imaging", Cell Cycle, Vol. 13, no. 6, pp. 953-960, delete "January 20, 2020" and insert --January 20, 2014--.

Signed and Sealed this
Thirtieth Day of May, 2023

Katherine Kelly Vidal
*Director of the United States Patent and Trademark Office*